United States Patent [19]

Wildman et al.

[11] 4,137,405

[45] Jan. 30, 1979

[54] ISOLATION OF ANTIBIOTIC CEPHAMYCIN C

[75] Inventors: George T. Wildman, Westfield; Rathin Datta, Princeton, both of N.J.

[73] Assignee: Merck & Co., Inc., Rahway, N.J.

[21] Appl. No.: 819,810

[22] Filed: Jul. 28, 1977

[51] Int. Cl.$^2$ .......................................... C07D 501/12
[52] U.S. Cl. ...................................... 544/20; 424/246
[58] Field of Search ............................................ 544/20

[56] References Cited

U.S. PATENT DOCUMENTS

| | | | |
|---|---|---|---|
| 3,467,654 | 9/1969 | McCormick et al. | 260/243 C |
| 3,709,880 | 1/1973 | Goegelman et al. | 544/20 |
| 3,725,400 | 4/1973 | Voser | 260/243 C |
| 3,853,863 | 12/1974 | Jackson et al. | 260/243 C |
| 3,914,157 | 10/1975 | Stapley et al. | 544/21 |
| 3,983,108 | 9/1976 | Pines | 544/20 |

OTHER PUBLICATIONS

Seika, Derwent Publication, 29281, Mar. 9, 1976.

*Primary Examiner*—Nicholas S. Rizzo
*Attorney, Agent, or Firm*—Richard A. Thompson; Hesna J. Pfeiffer; Julian S. Levitt

[57] ABSTRACT

Fermentation broths or impure solutions containing Cephamycin C, a substance having antibiotic activity against gram-negative and gram-positive microorganisms, are isolated using liquid anion exchange systems.

6 Claims, No Drawings

ISOLATION OF ANTIBIOTIC CEPHAMYCIN C

BACKGROUND OF THE INVENTION

The antibiotic, Cephamycin C, is obtained by growing strains of *Streptomyces lactamdurans* microorganism in suitable aqueous nutrient media under controlled conditions. The present invention is directed to the methods for recovering the antibiotic in substantially pure form.

A process for the preparation of the antibiotic Cephamycin C is reported in U.S. Pat. No. 3,914,157. Said process utilizes solid resin ion exchangers for the isolation of the antibiotic.

SUMMARY OF THE INVENTION

The novel process described herein uses water insoluble liquid anion exchangers which are dissolved in suitable organic solvents to transfer the Cephamycin C by the mechanism of ion exchange from the aqueous phase to the organic solvent followed by transfer of purified Cephamycin C from the liquid anion exchange/solvent system into suitable aqueous buffers, again by the mechanism of ion exchange. The use of conventional centrifugal extractors for the ion exchange extraction process lead to extremely fast mixing and phase separations thereby minimizing the time of isolation. This results in higher Cephamycin C recoveries than obtained by the use of conventional solid ion exchangers.

This invention relates to the method for recovering and purifying the antibiotic compound, Cephamycin C, having the following structural formula:

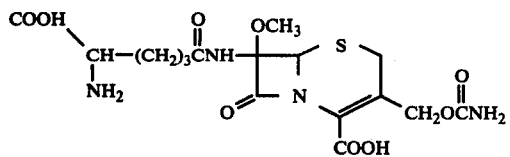

from fermentation broths in which the antibiotic is produced or from solutions containing partially purified antibiotic. This is achieved by contacting the fermentation broth in which the antibiotic is produced or a solution of partially purified antibiotic with liquid anion exchanger dissolved in an organic solvent to transfer the antibiotic into the liquid ion exchange system (forward extraction) and thereafter contacting the liquid ion exchange system which contains the antibiotic with an aqueous buffer solution to affect the transfer of the antibiotic into the aqueous buffer phase (back extraction).

The principal advantages of the liquid ion exchange process over the conventional solid ion exchange process are: 1) higher Cephamycin C recovery; and 2) the process can be operated in a truly continuous mode, thus giving the economic advantages of a continuous operation.

DESCRIPTION OF THE PREFERRED EMBODIMENTS

Cephamycin C is produced during the aerobic fermentation of suitable aqueous nutrient media, under controlled conditions, by a strain of *Streptomyces lactamdurans* capable of producing said compound such as NRRL 3802. Aqueous media, such as those employed for the production of other antibiotics are suitable for producing Cephamycin C. Such media contain sources of carbon, nitrogen and inorganic salts assimilable by the microorganism.

The production and characterization of the antibiotic Cephamycin C is described in U.S. Pat. No. 3,914,157 and is incorporated herein by reference.

The novel process utilized herein is based on liquid ion exchangers and an organic solvent. More particularly, the ion exchangers are liquid anion exchangers.

The anion exchanger is usually utilized in combination with an organic solvent as the extraction system. By the term "organic solvent" is meant an organic solvent or solvent mixture. The organic solvent should be one that has a moderately high dielectric constant.

By the term "moderately high dielectric constant" is meant a dielectric constant from about four to about twenty-four. Representative of such organic solvents having moderately high dielectric constants are straight and branched chain alcohols having from four to ten carbon atoms, straight and branched chain ketones having from four to eight carbon atoms and straight and branched chain esters having from four to ten carbon atoms.

Representative of said alcohols are n-butanol, isobutanol, pentanol, isopentanol, hexanol, heptanol and the like. Representative of said ketones are methyl ethyl ketone, methylisobutyl ketone and the like. Representative of said esters are ethyl acetate, butyl acetate and the like.

When a solvent mixture is utilized, one solvent with a high dielectric constant may be combined with a solvent having a low dielectric constant in order to obtain a solvent mixture having the desired dielectric constant.

By the term, "high dielectric constant" is meant a solvent having a dielectric constant from about twenty-five to about one hundred. By the term, "low dielectric constant" is meant less than four. Also, a mixture of solvents having moderately high dielectric constants may be utilized.

The liquid anion exchangers used are usually salts of strong anionic materials such as quaternary ammonium compounds. The liquid anion exchanger can be a salt of tricaprylyl methyl ammonium such as acetate, sulfate bicarbonate, propionate, phosphate, chloride, and the like or as the hydroxyl form.

The anion exchanger is usually utilized in a solvent solution wherein the anion exchanger is about 5 to 30% by volume.

The process for Cephamycin C isolation is carried out by contacting the alkaline pH (range from about 8.0–11.5) Cephamycin C-containing broth or solution with the liquid anion exchange system. After separation of the two liquid phases, the organic phase which now contains the Cephamycin C is back extracted with aqueous back extractants such as phosphoric acid, acetate, citrate, potassium chloride-hydrochloric acid buffers and the like, and the Cephamycin C transfers to the aqueous phase which is then separated from the organic phase.

The process described herein can be utilized with fermentation broths or solutions over a wide range of antibiotic concentrations. In general, the higher the antibiotic concentration, the more efficient the process. For instance, the antibiotic concentration can range from about two hundred milligrams per liter to about twenty grams per liter. However, this range is not intended to exclude solutions or broths which have been prepared to contain other concentrations of the antibiotic, Cephamycin C.

One such procedure comprises extracting Cephamycin C by contacting the aqueous phase with a strongly basic liquid anion exchange system at alkaline pH, from about 8.0–11.5, separating the phases (forward extraction), and then contacting the organic phase with a second aqueous phase and then separating the phases (back extraction).

The extractor system utilized in this invention can be any of those well known in the liquid-liquid extraction field. Those skilled in the art will appreciate that extractors of different design will have to be adjusted for optimum results.

EXAMPLE 1

A tube of lyophilized culture containing a Cephamycin C-producing *Streptomyces lactamdurans* is opened aseptically and 1.0 ml. of the contents suspended in a 250-ml. Hinton Erlenmeyer flask containing 210 ml. of sterile Medium B having the following composition:

| Medium B | |
|---|---|
| Primary Dried Yeast NF | 10 g./l. |
| Sodium hydroxide | to adjust pH to 7.0–7.1 |

The inoculated flask is shaken at 28° C. on a 250 rpm rotary shaker for 42 hours. Two ten-ml. portions of the Medium B stage 42-hour broth are removed asceptically. Each 10-ml. portion is mixed immediately with 400 ml. of Medium B contained in two 2-liter baffled Erlenmeyer flasks. These seed flasks are shaken at 28° C. on a 150 rpm rotary shaker for 24 hours.

Eight hundred ml. of the 24-hour Medium B broths contained in the 2-liter baffled Erlenmeyer flasks are used immediately to innoculate a 567-liter stainless steel fermentor containing 378 liters of Medium E having the following composition:

| Medium E | |
|---|---|
| Ardamine YEP (autolyzed yeast) | 10 g./l. |
| Mobil Par S | 2.5 ml./l. |
| Sodium hydroxide (25%) | to pH 7.0–7.1 |
| P-2000 (polyethylene glycol M.W. 1200–2100) | 0.76 ml./l. |

This tank is operated at 28° C. using an agitation rate of 134 rpm and an airflow (0–24 hours) of 2.5 cu. ft. per minute (cfm) then (24–34 hours final) 4.0 cfm. The pH and packed cell volume of the fermentation are monitored at 4-hour intervals and are tabulated in the following table.

| Age | pH | Cell Volume |
|---|---|---|
| 0 | 6.9 | 0 |
| 14 | 7.0 | 0.5 |
| 18 | 7.1 | 1.0 |
| 22 | 7.15 | 2.0 |
| 26 | 7.5 | 5.0 |
| 30 | 7.55 | 8.0 |
| 34 | 7.7 | 12.0 |

Three hundred seventy-eight liters of the above 34-hour broth contained in the 567-liter stainless steel fermentor are used immediately to inoculate a 5670-liter stainless steel fermentor containing 3232 liters of Medium F having the following composition:

| Medium F | |
|---|---|
| Ardamine YEP (autolyzed yeast) | 13.2 g./l. |
| Primary dried yeast | 13.2 g./l. |
| Cerelose (dextrose monohydrate) | 13.2 g./l. |
| Sodium Hydroxide (25%) | to pH 7.0–7.1 |
| p-2000 (polyethlene glycol M.W. 200–2100) | 0.21 ml./l. |

This 5670-liter fermentor is operated at 28° C. using an agitation rate of 234 rpm and airflow (0–2 hours) 15 cfm and (2–22 hours final) 30 cfm. The pH and cell volume of the fermentation are monitored at 4-hour intervals and are tabulated in the following table.

| Age | pH | Cell Volume |
|---|---|---|
| 0 | 7.0 | 4 |
| 4 | 6.9 | 5 |
| 8 | 7.0 | 5 |
| 12 | 7.2 | 6 |
| 16 | 7.4 | 9 |
| 20 | 7.3 | 16 |
| 22+ | 7.4 | 24 |

Three thousand three hundred thirty-two liters of the above 22-hour broth are used immediately to inoculate a 75,600-liter stainless steel fermentor containing 54,224 liters of Medium G broth containing the following quantities of material:

| Medium G - Portion I | Amount 0–24 hours | Final Conc. |
|---|---|---|
| Cornsteep (Cornsteep water) | 1909 kgs. | 33 g./l. |
| Feathermeal | 580 kgs. | 10 g./l. |
| Meat meal (55 minimum protein) | 1160 kgs. | 20 g./l. |
| Dimethylformamide | 542 kgs. | |
| Glycine | 57.8 kgs. | 1.0 g./l. |
| Magnesium sulfate heptahydrate | 29 kgs. | 0.5 g./l. |
| Polyethylene glycol (M.W. 1200–2000) | 6.6 kgs. | 0.15 ml./l. |
| Sodium hydroxide (25%) | to pH 7.3 | |

The above Portion I of Medium G is sterilized and then a second three-part portion of materials is added immediately to the 75,600-liter fermentor having the following composition.

Part A - In a 5670-liter stainless steel vessel, 1735 kgs. of dextrose monohydrate are made up to 3232 liters.

Part B - In a 576-liter stainless steel vessel, 57.8 kgs. of DL lysine-monohydrochloride are made up to 378 liters and adjusted to pH 7.0–7.1 using 25% sodium hydroxide.

Part C - In a 5676-liter stainless steel vessel, 28.9 kgs. of 1,3-diaminopropane (free base) are made up to 3232 liters and adjusted to pH 7.0–7.1 using concentrated reagent grade hydrochloric acid.

Parts B and C are combined and added to the above-mentioned Medium G - Portion I. Part A is added immediately after Parts B and C.

A third portion of materials is added to the 75,600-liter fermentor after 24 hours. This third portion of materials has two parts having the following composition.

Part D - In a 576-liter stainless steel vessel 90.8 kgs. of sodium thiosulfate pentahydrate are made up to 378 liters.

Part E - In a 5670-liter stainless steel vessel, 1735 kgs. of dextrose monohydrate are made up to 3232 liters.

This tank is operated at 100 rpm and an airflow rate of 600 cfm using a temperature of 28.0° C. for 96 to 100 hours.

After harvest, the fermentation broth is filtered using a rotary pressure filter and admix. The filtered broth, at about 5° C., is mixed continuously with 2.5 N sodium hydroxide to bring the broth pH to 11.5 using an in-line mixer. The alkaline broth is then pumped at a rate of 36 gallons per minute (gpm) to a Podbielniak (model D-36) centrifugal extractor where it is contacted with 30% v/v tricaprylyl methyl ammonium, acetate cycle, in n-butanol which is being fed to the extractor at 36 gpm. In the Podbielniak extractor, the two solutions are intimately mixed and the anion exchange reaction occurs at about pH 10.7 between the acetate ion of the tricaprylyl methyl ammonium moiety and the carboxylate anion form of Cephamycin C resulting in the transfer of Cephamycin C from the aqueous phase to the solvent phase. The two phases are then efficiently separated by the centrifugal forces operative in the Podbielniak extractor. The Cephamycin C-containing solvent phase, the rich anion exchanger-solvent stream is then pumped to a second Podbielniak extractor where it is contacted with an aqueous back extractant, 4.25% v/v phosphoric acid, for the back extraction of Cephamycin C from the solvent phase to this second aqueous phase. The back extractant is fed at the rate of 36 gpm to the Podbielniak being used for the back extraction.

About 98% of the Cephamycin C is extracted from the broth into the quaternary ammonium/n-butanol phase in the first Podbielniak extractor and about 95% of the Cephamycin C is extracted from the quaternary ammonium/n-butanol phase into the aqueous buffer using the second Podbielniak extractor. Substantial purification of the Cephamycin C results. Purification is the ratio of Cephamycin C concentration to the total dissolved organic solids concentration. In this instance, the purity is increased ten-fold.

What is claimed is:

1. A process for recovering the antibiotic Cephamycin C from fermentation broths or solutions containing said antibiotic wherein ion exchangers are utilized, the improvement being utilizing a water insoluble quarternary ammonium liquid anion exchanger dissolved in an organic solvent having a dielectric constant from about 4 to about 24.

2. A process for recovering the antibiotic Cephamycin C from fermentation broths or solutions containing said antibiotic which comprises contacting said broths or solutions with a water insoluble quarternary ammonium liquid anionic exchanger dissolved in an organic solvent having a dielectric constant from about 4 to about 24 to transfer the antibiotic into said liquid anionic exchanger (forward extraction) and thereafter contacting said liquid anionic exchanger with an aqueous buffer to affect the transfer of said antibiotic into the aqueous buffer phase (back extraction).

3. A process according to claim 1 wherein the liquid anion exchanger is a salt selected from the group of tricaprylyl methyl ammonium acetate, tricaprylyl methyl ammonium propionate, tricaprylyl methyl ammonium phosphate, tricaprylyl methyl ammonium sulfate or tricaprylyl methyl ammonium bicarbonate.

4. A process according to claim 1 wherein the solvent is selected from alcohols containing from four to ten carbon atoms.

5. A process according to claim 1 wherein the solvent is selected from ketones containing from four to eight carbon atoms.

6. A process according to claim 1 wherein the solvent is selected from esters containing from four to ten carbon atoms.